(12) United States Patent
Su et al.

(10) Patent No.: US 7,829,574 B2
(45) Date of Patent: Nov. 9, 2010

(54) SUBSTITUTED QUINAZOLINE COMPOUNDS AND THEIR USE IN TREATING ANGIOGENESIS-RELATED DISEASES

(75) Inventors: Wei-Guo Su, Shanghai (CN); Weihan Zhang, Shanghai (CN); Xiaoqiang Yan, Shanghai (CN); Yumin Cui, Shanghai (CN); Yongxin Ren, Shanghai (CN); Jifeng Duan, Shanghai (CN)

(73) Assignee: Hutchison MediPharma Enterprises Limited (BS)

( * ) Notice: Subject to any disclaimer, the term of this patent is extended or adjusted under 35 U.S.C. 154(b) by 0 days.

(21) Appl. No.: 12/118,019

(22) Filed: May 9, 2008

(65) Prior Publication Data
US 2009/0281130 A1  Nov. 12, 2009

(51) Int. Cl.
*A61K 31/517* (2006.01)

(52) U.S. Cl. .................... 514/266.24; 544/287; 549/471
(58) Field of Classification Search ............ 514/266.24; 544/287; 549/471
See application file for complete search history.

(56) References Cited

U.S. PATENT DOCUMENTS

| 5,457,105 | A | 10/1995 | Barker |
| 6,235,741 | B1 | 5/2001 | Bilodeau et al. |
| 6,723,726 | B1 | 4/2004 | Cockerill et al. |
| 2003/0149041 | A1 | 8/2003 | Erickson et al. |
| 2004/0092750 | A1 | 5/2004 | Hasegawa et al. |
| 2005/0137395 | A1 | 6/2005 | Hong et al. |
| 2006/0247262 | A1 | 11/2006 | Baenteli et al. |
| 2007/0208056 | A1 | 9/2007 | Carter et al. |
| 2008/0033000 | A1 | 2/2008 | Chang |

FOREIGN PATENT DOCUMENTS

| EP | 1265874 | | 12/2002 |
| EP | 1 154 774 B1 | | 6/2005 |
| EP | 1154774 | | 6/2005 |
| NZ | 535109 | | 5/2006 |
| WO | WO 02/30924 | * | 4/2002 |
| WO | 03/063794 | | 8/2003 |
| WO | 2004/014382 | | 2/2004 |
| WO | 2005/009978 | | 2/2005 |
| WO | 2005/026158 | | 3/2005 |
| WO | 2005/063739 | | 7/2005 |
| WO | WO 2005/063739 A1 | | 7/2005 |
| WO | 2006/071017 | | 7/2006 |
| WO | 2006/071079 | | 7/2006 |
| WO | 2006/138304 | | 12/2006 |
| WO | WO 2007/066181 A2 | | 6/2007 |
| WO | WO 2009/036055 | * | 3/2009 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Verma et al. "Substituted Aminobenzimidazole Pyrimidines as Cyclin-Dependent Kinase Inhibitors" Bioorganic & medicinal Chemistry Letters 15 92005) 1973-1977, 5 pages.
Zhang et al. "Discovery of EGFR Selective 4,6-Disubstituted Pyrimidines from a Combinatorial Kinase-Directed Heterocycle Library," J.Am. Chem. Soc. 2006, 128, 2182-2183.
Harris et al., "Three-point variation of a gefinitib quinazoline core," *Tetrahedron Letters*, 50:1600-1602 (2009).
Nakamura et al., "KRN951, a Highly Potent Inhibitor of Vascular Endothelial Growth Factor Receptor Tyrosine Kinases, Has Antitumor Activities and Affects Functional Vascular Properties," *Cancer Research*, 66:9134-9142 (2006).

* cited by examiner

*Primary Examiner*—James O Wilson
*Assistant Examiner*—Douglas M Willis
(74) *Attorney, Agent, or Firm*—Finnegan, Henderson, Farabow, Garrett & Dunner, LLP

(57) ABSTRACT

Substituted quinazoline compounds of the following formula:

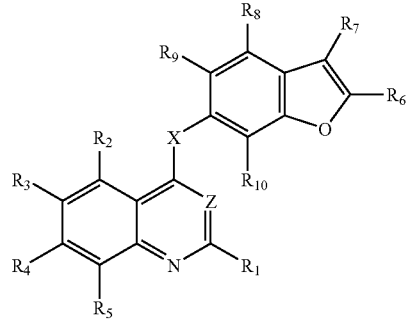

wherein $R_1$, $R_2$, $R_3$, $R_4$, $R_5$, $R_6$, $R_7$, $R_8$, $R_9$, $R_{10}$, and X are defined herein. It also discloses a pharmaceutical composition containing one of these compounds.

17 Claims, No Drawings

SUBSTITUTED QUINAZOLINE COMPOUNDS AND THEIR USE IN TREATING ANGIOGENESIS-RELATED DISEASES

BACKGROUND

Angiogenesis is a physiological process of growing new blood vessels from pre-existing vessels. It takes place in a healthy subject to heal wounds, i.e., restoring blood flow to tissues after injury or insult.

Excessive angiogenesis may be triggered by certain pathological conditions such as cancer, age-related macular degeneration, and chronic inflammatory disease. As a result, new blood vessels feed diseased tissues and destroy normal tissues. In cancer, new blood vessels also allow tumor cells to escape into the circulation and lodge in other organs.

Vascular endothelial growth factor (VEGF), a homodimeric glycoprotein, and its receptors, e.g., kinase insert domain receptor (KDR), constitute an important angiogenic pathway. Studies have shown that inhibition of KDR resulted in endothelial cell apoptosis and, thus, suppression of angiogenesis. See Rubin M. Tuder, Chest, 2000; 117: 281. KDR inhibitors are therefore potential candidates for treating an angiogenesis-related disorder.

SUMMARY

This invention is based on the discovery that a number of quinazoline compounds inhibit the activity of KDR.

One aspect of this invention relates to quinazoline compounds of the following formula (I):

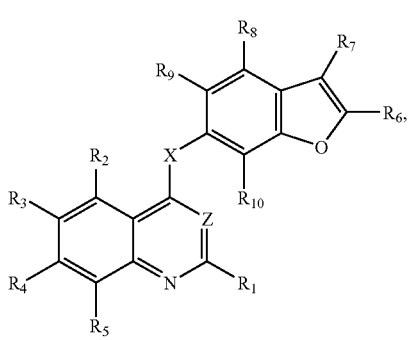

in which each of $R_1$, $R_2$, $R_3$, $R_4$, $R_5$, $R_6$, $R_7$, $R_8$, $R_9$, and $R_{10}$, independently, is H, halo nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl, or $R_3$ and $R_4$, together with the carbon atoms to which they are attached, form a 4- to 7-membered saturated, unsaturated, or aromatic ring, optionally containing 1-3 hetero atoms selected from N, O and S; X is O, S, or NR, wherein R is H, alkyl, alkenyl, alkynyl, aryl, cycloalkyl, heterocycloalkyl, heteroaryl, alkylcarbonyl, alkoxycarbonyl, aminocarbonyl, or aminosulfonyl; and Z is N or C—CN.

The above-described compounds may have one or more of the following features: X is O, NH, or N—$CH_3$; $R_7$ is —C(O)$NR_aR_b$, each of $R_a$ and $R_b$, independently, being H, alkyl, alkenyl, alkynyl, aryl, cycloalkyl, heterocycloalkyl, or heteroaryl, or $R_a$ and $R_b$, together with the nitrogen atom, represent a 3-8 membered ring containing 1-3 heteroatoms; $R_6$ is alkyl (e.g., methyl); or each of $R_3$ and $R_4$ is alkoxy (e.g., methoxy). In one subset of the above compounds each of $R_a$ and $R_b$, independently, is H, alkyl (e.g., methyl), or cycloalkyl (e,g, cyclopropyl).

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl.

The term "alkenyl" herein refers to a $C_{2-10}$ straight or branched hydrocarbon, containing one or more C=C double bonds. Examples of alkenyl groups include, but are not limited to, vinyl, 2-propenyl, and 2-butenyl.

The term "alkynyl" herein refers to a $C_{2-10}$ straight or branched hydrocarbon, containing one or more C≡C triple bonds. Examples of alkynyl groups include, but are not limited to, ethynyl, 2-propynyl, and 2-butynyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocycloalkyl" refers to a nonaromatic 3-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl. Heterocycloalkyl can be a saccharide ring, e.g., glucosyl.

Alkyl, alkenyl, alkynyl, cycloalkyl, heterocycloalkyl, aryl, heteroaryl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, heterocycloalkyl, in which alkyl, alkenyl, alkynyl, alkyloxy, aryl, heteroaryl cycloalkyl, and heterocycloalkyl may further substituted.

The quinazoline compounds described above include their pharmaceutically acceptable salts, solvate, and prodrug, if applicable.

Examples of the compounds of this invention are shown below:

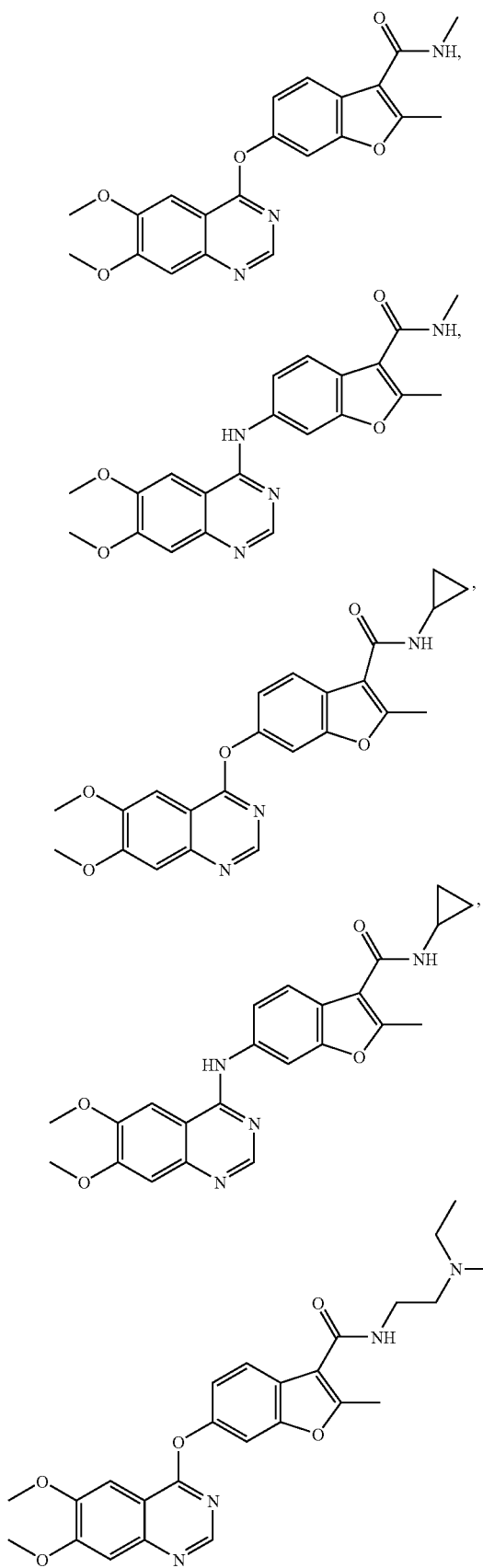
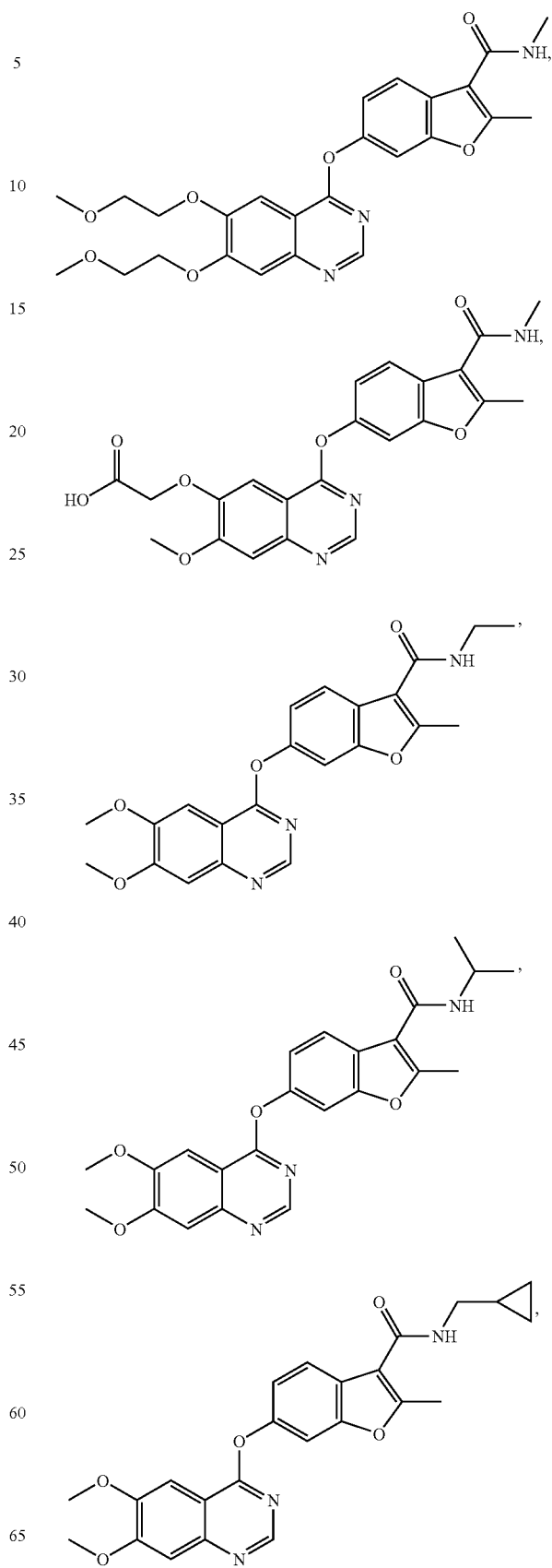

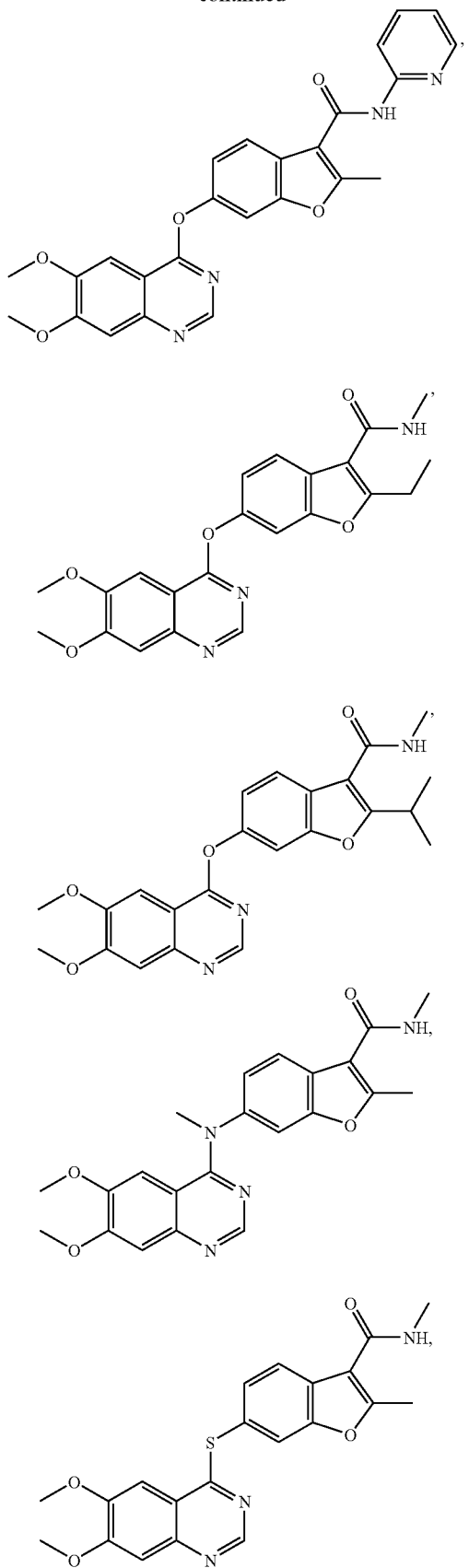
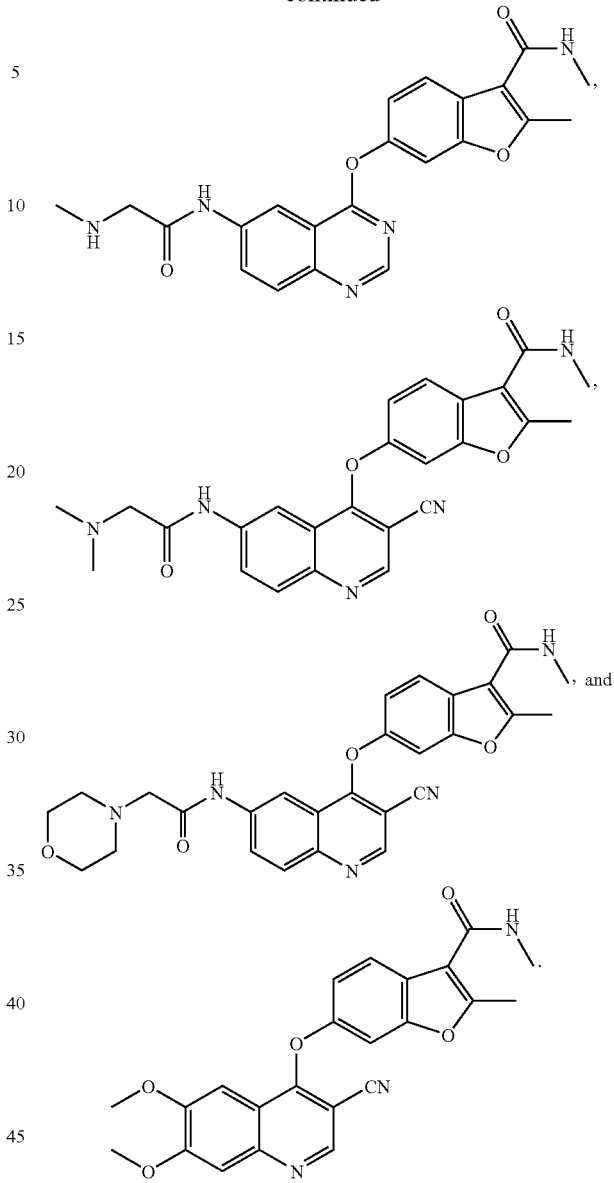

Another aspect of this invention relates to a method of inhibiting angiogenesis by administrating to a subject in need thereof an effective amount of a quinazoline compound of formula (I) as described above.

Yet another aspect of this invention relates to a method of treating an angiogenesis-related disorder (e.g., cancer, age-related macula degeneration, or chronic inflammatory disease). The method includes administering to a subject having an angiogenesis-related disorder an effective amount of one or more of the quinazoline compounds of this invention. Examples of cancer include, but are not limited to, lung cancer, colon cancer, breast cancer, ovarian cancer, prostate cancer, stomach cancer, kidney cancer, liver cancer, brain cancer, bone cancer, and leukemia. Examples of chronic inflammatory disorders include, but are not limited to, inflammatory bowel disease (such as Crohn's disease and ulcerative colitis), rheumatoid arthritis, lupus, psoriasis, and diabetes mellitus.

Also within the scope of this invention are (1) a composition containing one or more of the quinazoline compounds described above and a pharmaceutically acceptable carrier for use in treating an angiogenesis-related disorder (e.g., such cancer or age-related macular degeneration, or chronic inflammatory disease) and (2) use of one or more of the quinazoline compounds for the manufacture of a medicament for treating the disorder.

The details of one or more embodiments of the invention are set forth in the description below. Other features, objects and advantages of the invention will be apparent from the description and from the claims.

DETAILED DESCRIPTION

The quinazoline compounds of this invention can be synthesized from commercially available starting materials by methods well known in the art. For example, as shown in scheme 1 below, one can couple a suitable 4-chloro-quinazoline derivative with a benzofuran compound to obtain a compound of this invention.

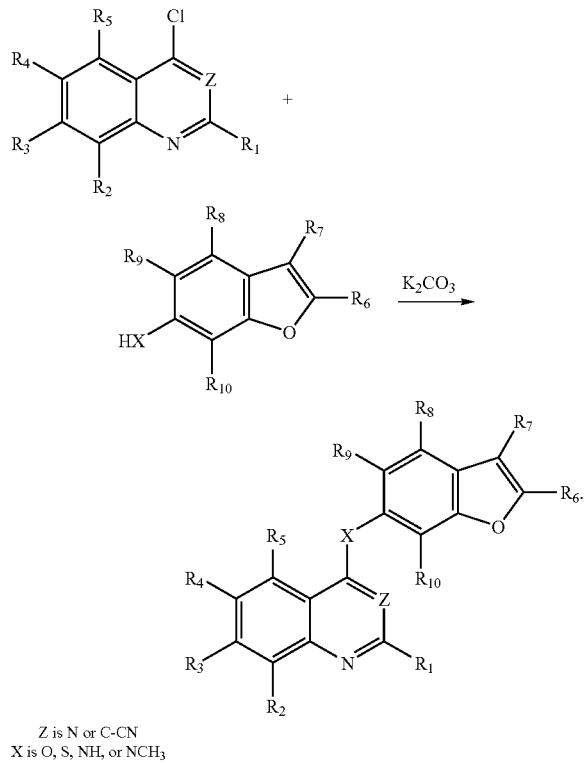

Scheme 1

Z is N or C-CN
X is O, S, NH, or NCH$_3$

The compound thus obtained can be further modified at their peripheral positions to provide other compounds of this invention.

Synthetic chemistry transformations useful in synthesizing desirable quinazoline compounds are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the compounds can be purified by column chromatography, high performance liquid chromatography, crystallization, or other suitable methods.

The quinazoline compounds of this invention, when contacting with KDR, inhibit this receptor's activity. An effective amount of one or more of these compounds can be therefore used to inhibit angiogenesis and treat a subject having an angiogenesis-related disorder.

The term "an effective amount" refers to the amount of a quinazoline compound that is required to confer the intended effect in the subject. Effective amounts may vary, as recognized by those skilled in the art, depending on route of administration, excipient usage, and the possibility of co-usage with other agents. The term "treating" refers to administering one or more of the above-described quinazoline compounds to a subject that has an angiogenesis-related disorder, or has a symptom of the disorder, or has a predisposition toward the disorder, with the purpose to cure, heal, alleviate, relieve, alter, remedy, ameliorate, improve, or affect the disorder, the symptoms of the disorder, or the predisposition toward the disorder.

To practice this method, a composition having one or more of the quinazoline compounds of this invention can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond and about 70% by weight white soft paraffin.

A carrier in a pharmaceutical composition must be "acceptable" in the sense that it is compatible with active ingredients of the formulation (and preferably, capable of stabilizing it) and not deleterious to the subject to be treated. For example, solubilizing agents, such as cyclodextrins (which form specific, more soluble complexes with one or more of active quinazoline compounds of the extract), can be utilized as pharmaceutical excipients for delivery of the active ingredients. Examples of other carriers include colloidal silicon dioxide, magnesium stearate, cellulose, sodium lauryl sulfate, and D&C Yellow #10.

Suitable in vitro assays can be used to preliminarily evaluate the efficacy of the above-described quinazoline compounds in inhibiting the activity of KDR or inhibiting the activity of VEGF. The compounds can further be examined for its efficacy in treating an angiogenesis-related disorder by in vivo assays. For example, the compounds can be administered to an animal (e.g., a mouse model) having cancer and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever.

Example 1

Synthesis of 6-(6,7-dimethoxyquinazolin-4-yloxy)-N,2-dimethylbenzofuran-3-carboxamide

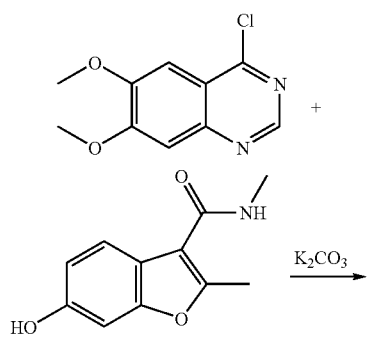

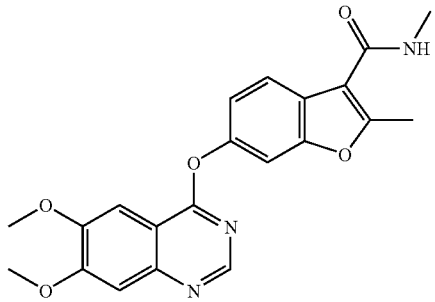

To a solution of 4-chloro-6,7-dimethoxyquinazoline (1 equiv.) in 2 ml $CH_3CN$ were added 6-hydroxy-N,2-dimethylbenzofuran-3-carboxamide (1 equiv.) and $K_2CO_3$ (1.5 equiv.). The mixture was refluxed under stirring for 10 hr. After the solvent was evaporated, the residue was washed with water, dried over $MgSO_4$, filtered, concentrated, and purified by column chromatography to give the title compound in a yield of 85%.

$^1$H NMR (DMSO-$d_6$, 400 MHz) δ: 2.49 (s, 3H), 2.81 (d, J=8.4 Hz, 3H,10), 3.97 (s, 3H), 3.98 (s, 3H), 7.24 (dd, J=2.0, 8.4 Hz, 1H), 7.38 (s, 1H), 7.58 (s, 1H), 7.61 (d, J=2.0 Hz, 1H), 7.79 (d, J=8.4 Hz, 1H), 7.96 (m, 1H), 8.52 (s, 1H).

MS(m/e): 394.1 (M+1).

Example 2

Synthesis of 6-(6,7-dimethoxyquinazolin-4-ylamino)-N,2-dimethylbenzofuran-3-carboxamide This compound was prepared in a manner similar to that described in Example 1.

$^1$H NMR (DMSO-$d_6$, 400 MHz) δppm: 2.74 (s, 3H), 2.83 (d, J=8.4 Hz, 3H), 3.95 (s, 3H), 3.98 (s,3H), 7.20 (s, 1H), 7.60 (dd, J=8.4, 2.0 HZ, 1H), 7.75 (d, J=8.4 Hz,1H), 7.89 (s, 2H), 8.22 (d, J=2 Hz, 1H), 8.50 (s, 1H), 9.65 (s, 1H).

MS(m/e): 393.15 (M+1).

Example 3

Synthesis of N-(2-(diethylamino)ethyl)-6-(6,7-dimethoxyquinazolin-4-yloxy)-2-methylbenzofuran-3-carboxamide

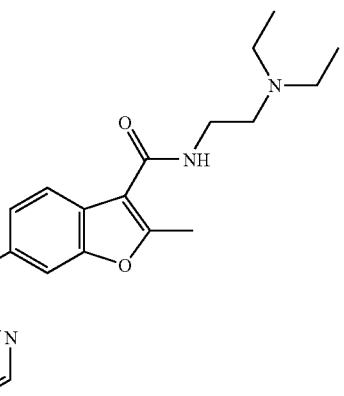

This compound was prepared in a manner similar to that described in Example 1.

$^1$H NMR (DMSO-$d_6$, 400 MHz): 8.54 (s, 1H), 7.85 (bs, 1H), 7.84-7.83 (d, J=2.8 Hz, 1H), 7.66 (s, 1H), 7.60 (s, 1H), 7.41 (s, 1H), 7.29-7.27 (d, J=8.0 Hz, 1H), 4.00 (d, J=2.8 Hz, 6H), 2.67 (s, 3H), 2.64-2.51 (m, 8H), 1.02 (bs, 6H).

MS (m/e): 479.5 (M+1).

Example 4

Synthesis of N-cyclopropyl-6-(6,7-dimethoxyquinazolin-4-yloxy)-2-methylbenzofuran-3-carboxamide

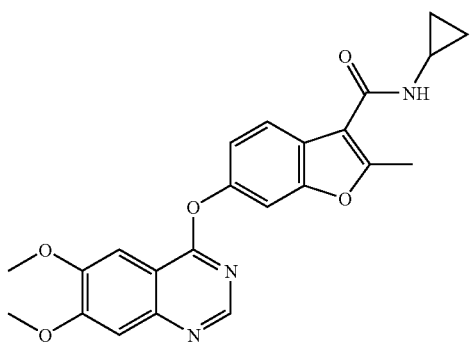

This compound was prepared in a manner similar to that described in Example 1.

$^1$H NMR (DMSO-$d_6$, 400 MHz): 8.53 (s, 1H), 8.22 (s, 1H), 7.72-7.70 (d, J=8.8 Hz, 2H), 7.63-7.61 (d, J=8.0 Hz, 1H), 7.41 (s, 1H), 7.26-7.24 (d, J=8.0 Hz, 1H), 4.00 ((d, J=2.8 Hz, 6H), 2.88 (bs, 1H), 2.61 (s, 3H), 0.74-0.73 (d, J=5.6 Hz, 2H), 0.63 (bs, 2H).

MS (m/e): 420.4 (M+1).

Example 5

Synthesis of 6-(6,7-bis(2-methoxyethoxy)quinazolin-4-yloxy)-N,2-dimethylbenzofuran-3-carboxamide

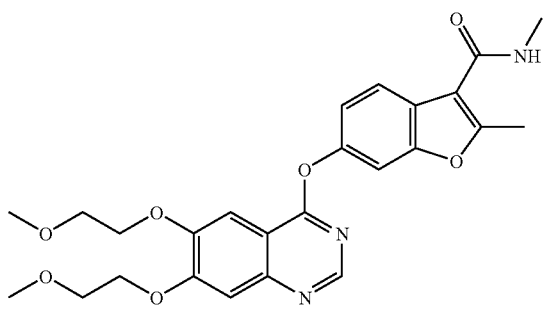

This compound was prepared following the procedure described in Example 1.

MS(m/e): 482.2 (M+1).

Example 6

Inhibition of KDR Kinase Activity

Inhibition of KDR kinase activity by test compounds was assessed using a Z'-LYTE™ Tyr1 Peptide assay kit (Invitrogen, Carlsbad, Calif., U.S.A., Cat. PV3190). The assay was performed according to the procedures recommended by the manufacturer.

Briefly, each test compound in DMSO (10 mM) was diluted to 1:4 with distilled water containing 8% DMSO. The solution was placed in a test well and three control wells (C1, C2, and C3) at 2.5 μl/well in a black 384-well plate (Thermo labsystems, Cambridge, U.K., Cat. 7805). The Z'-LYTE™ Tyr1 peptide, a coumarin-fluorescein double-labeled peptide substrate, was mixed with a KDR catalytic domain (Invitrogen, Cat. PV3660). 5 μl of the kinase/peptide mixture was added to each of the test, C1, and C2 wells, but not C3 (final concentration: 0.3 μg/ml of Kinase, 2 μM of peptide). 5 μl of phosphor-Tyr1 peptide was added to the C3 well. 2.5 μl of 40 μM ATP was added to the test and C2 wells and 2.5 μl of 1.33× kinase buffer (1× buffer: 50 mM HEPES, pH7.5, 0.01% Brij-35, 5 mM MgCl$_2$, 5 mM MnCl$_2$, and 1 mM EGTA) was added to the C1 and C3 wells. The plate was briefly spun at 1000 rpm to allow the solutions to be well mixed at the bottom of the wells and then sealed and shaken at 250 rpm and 25° C. for 1 hour.

A development reagent was diluted to 1:128 following the instructions provided by the manufacturer. 5 μl of the diluted development reagent was added to each well. The plate was spun at 1000 rpm to allow the solutions to be well mixed at the bottom of the wells, and then sealed and shaken at 250 rpm and 25° C. for 1 hour.

5 μl of a stop reagent was added to each well. The plate was spun at 1000 rpm and then sealed at 250 rpm and 25° C. for 2 minutes. The fluorescein emission of the solution at each well was measured by a Victor™3 micro-plate reader at Excitation 400 nm/Emission 445 nm and 520 nm. The emission ratio and phosphorylation ("Phos.") percentage were calculated by the following equations:

$$\text{Emission Ratio} = \frac{\text{Coumarin Emission (445 nm)}}{\text{Fluorescein Emission (520 nm)}}$$

$$\% \text{ Phosphorylation} = 1 - \frac{(\text{Emission Ratio} \times F_{100\%}) - C_{100\%}}{(C_{0\%} - C_{100\%}) + [\text{Emission Ratio} \times (F100\% - F0\%)]}$$

where $C_{100\%}$=Average Coumarin emission signal of the 100% Phos. Control $C_{0\%}$=Average Coumarin emission signal of the 0% Phos. Control $F_{100\%}$=Average fluorescein emission signal of the 100% Phos. Control $F_{0\%}$=Average fluorescein emission signal of the 0% Phos. Control The inhibition ratio was calculated as follows:

Inhibition %=(Phos. in C2 well−Phos. in test well)/(Phos. in C2 well)×100% IC$_{50}$ (concentration required to inhibit KDR kinase activity by 50%) values were calculated based inhibition ratios thus obtained.

The result showed that Compounds 1-5 inhibited the activity of KDR. The tested compounds had IC$_{50}$ values ranging from 0.001 to 10 μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention can be made and used to practice this invention. Thus, other embodiments are also within the claims.

What is claimed is:

1. A compound of the following formula:

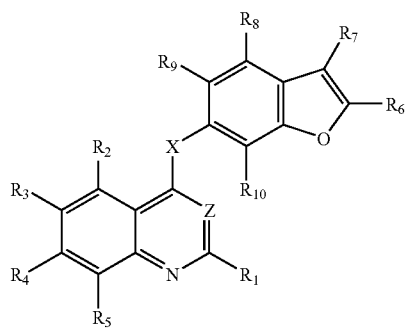

in which
each of $R_1$, $R_2$, $R_3$, $R_4$, $R_5$, $R_8$, $R_9$, and $R_{10}$, independently, is H, halo, amino, hydroxy, alkyl, alkenyl, alkynyl, heterocycloalkyl, alkoxy, alkylthio,-carboxy, alkoxycarbonyl, carbonylamino, or sulfonylamino, or $R_3$ and $R_4$, together with the carbon atoms to which they are attached, form a 4- to 7-membered saturated, unsaturated, or aromatic ring, optionally containing 1-3 hetero atoms selected from N, O and S;
$R_6$ is alkyl;
$R_7$ is alkoxycarbonyl, aminocarbonyl, or aminosulfonyl;
X is O; and
Z is N;
wherein each of alkyl, alkenyl, alkynyl, heterocycloalkyl, and alkoxy is optionally substituted with at least one substituent chosen from halo, hydroxyl, amino, cyano, nitro, mercapto, alkoxycarbonyl, amido, carboxy, alkanesulfonyl, alkylcarbonyl, carbamido, carbamoyl, carboxyl, thioureido, thiocyanato, sulfonamido, alkyl, alkenyl, alkynyl, alkoxy, aryl, heteroaryl, cycloalkyl, and heterocycloalkyl.

2. A compound of the following formula:

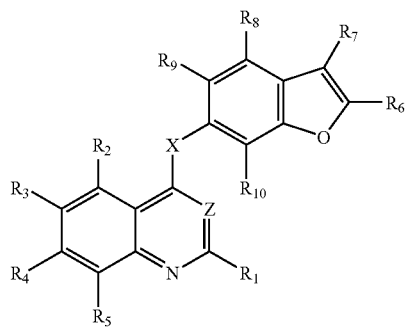

wherein
each of $R_1$, $R_2$, $R_3$, $R_4$, $R_5$, $R_8$, $R_9$, and $R_{10}$, independently, is H, halo, amino, hydroxy, alkyl, alkenyl, alkynyl, heterocycloalkyl, alkoxy, alkylthio,-carboxy, alkoxycarbonyl, carbonylamino, or sulfonylamino, or $R_3$ and $R_4$, together with the carbon atoms to which they are attached, form a 4- to 7-membered saturated, unsaturated, or aromatic ring, optionally containing 1-3 hetero atoms selected from N, O and S;
$R_6$ is alkyl;
$R_7$ is —C(O)NR$_a$R$_b$, each of R$_a$ and R$_b$, independently, being H, alkyl, alkenyl, alkynyl, aryl, cycloalkyl, heterocycloalkyl, or heteroaryl, or R$_a$ and R$_b$, together with the nitrogen atom to which they are attached, represent a 3-8 membered ring containing 1-3 heteroatoms;
X is O; and
Z is N;
wherein each of alkyl, alkenyl, alkynyl, cycloalkyl, heterocycloalkyl, aryl, heteroaryl, and alkoxy is optionally substituted with at least one substituent chosen from halo, hydroxyl, amino, cyano, nitro, mercapto, alkoxycarbonyl, amido, carboxy, alkanesulfonyl, alkylcarbonyl, carbamido, carbamoyl, carboxyl, thioureido, thiocyanato, sulfonamido, alkyl, alkenyl, alkynyl, alkoxy, aryl, heteroaryl, cycloalkyl, and heterocycloalkyl.

3. The compound of claim 1, wherein $R_6$ is optionally substituted methyl.

4. The compound of claim 3, wherein $R_6$ is methyl.

5. The compound of claim 1, wherein each of $R_3$ and $R_4$ is optionally substituted alkoxy.

6. The compound of claim 2, wherein each of $R_3$ and $R_4$ is optionally substituted alkoxy.

7. The compound of claim 2, wherein each of R$_a$ and R$_b$, independently, is H, optionally substituted alkyl, or optionally substituted cycloalkyl.

8. The compound of claim 7, wherein R$_a$ is H and R$_b$ is optionally substituted methyl.

9. The compound of claim 7, wherein each of $R_3$ and $R_4$ is methoxy.

10. A compound of the formula:

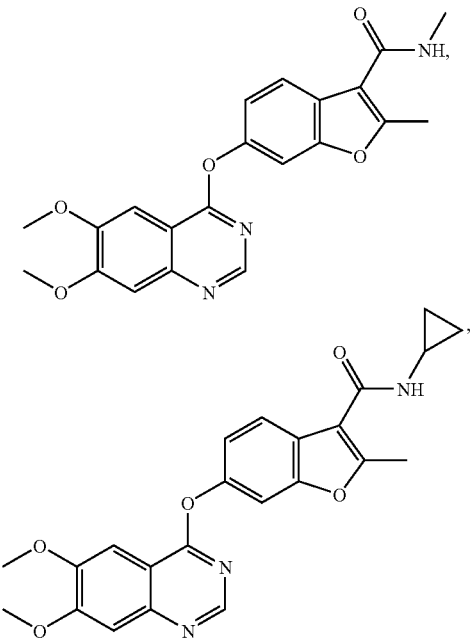

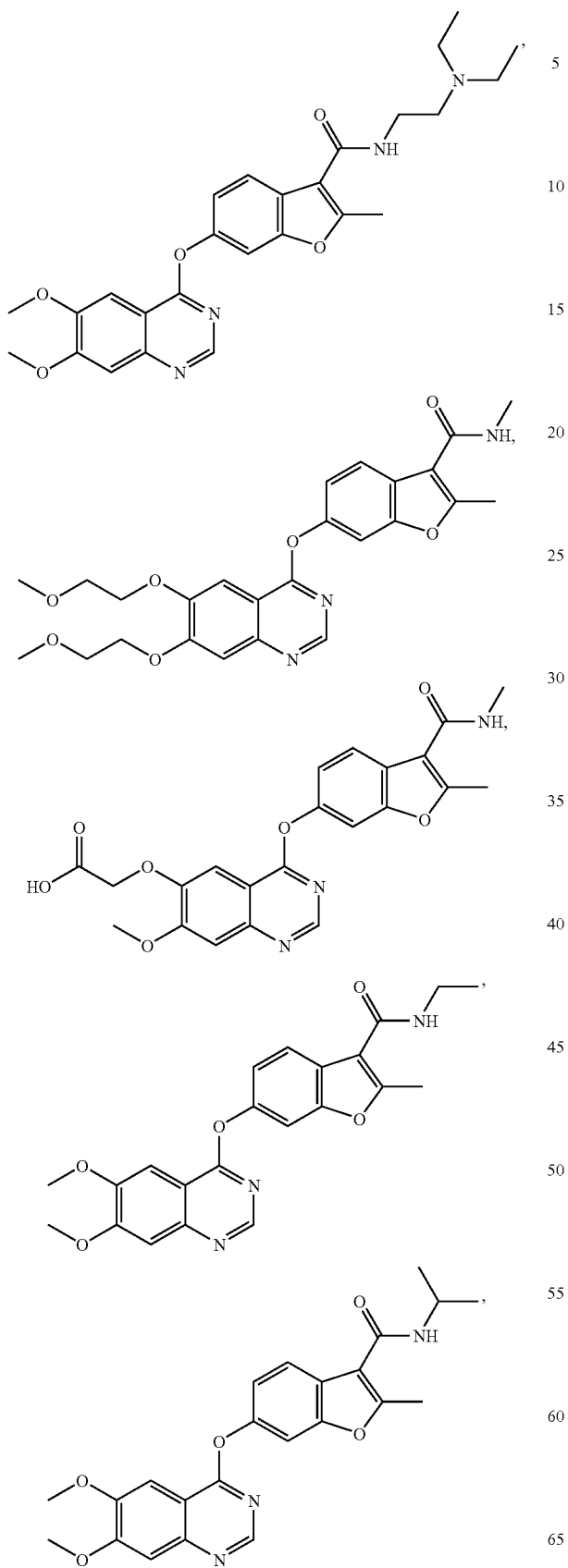
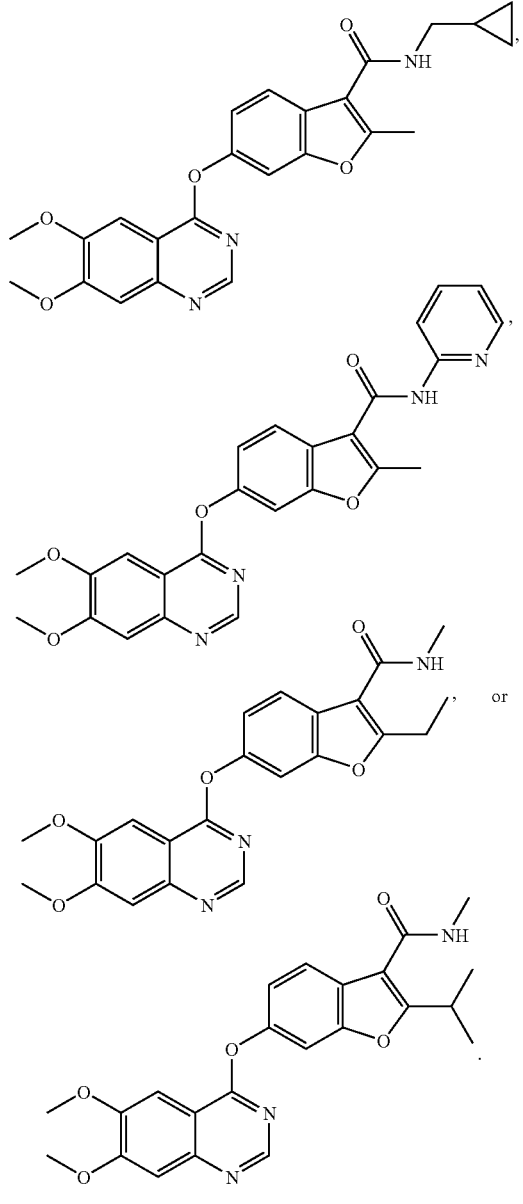
11. A pharmaceutical composition comprising a compound of the following formula:
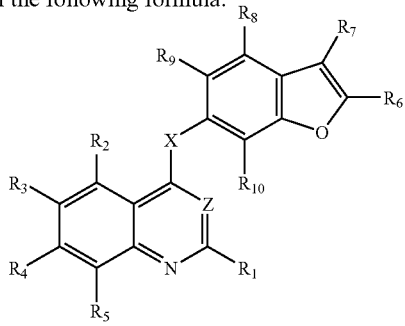
wherein
each of $R_1$, $R_2$, $R_3$, $R_4$, $R_5$, $R_8$, $R_9$, and $R_{10}$, independently, is H, halo, amino, hydroxy, alkyl, alkenyl, alkynyl, heterocycloalkyl, alkoxy, alkylthio,-carboxy, alkoxycarbonyl, carbonylamino, or sulfonylamino, or $R_3$ and $R_4$, together with the carbon atoms to which they are attached, form a 4- to 7-membered saturated, unsaturated, or aromatic ring, optionally containing 1-3 hetero atoms selected from N, O and S;

$R_6$ is alkyl;

$R_7$ is alkoxycarbonyl, aminocarbonyl, or aminosulfonyl;

X is O; and

Z is N;

wherein each of alkyl, alkenyl, alkynyl, heterocycloalkyl, and alkoxy is optionally substituted with at least one substituent chosen from halo, hydroxyl, amino, cyano, nitro, mercapto, alkoxycarbonyl, amido, carboxy, alkanesulfonyl, alkylcarbonyl, carbamide, carbamoyl, carboxyl, thioureido, thiocyanato, sulfonamido, alkyl, alkenyl, alkynyl, alkyloxy, aryl, heteroaryl, cycloalkyl, and heterocycloalkyl;

and a pharmaceutically acceptable carrier.

12. A pharmaceutical composition comprising a compound of the formula:

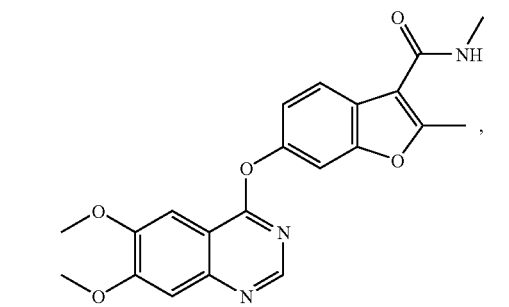

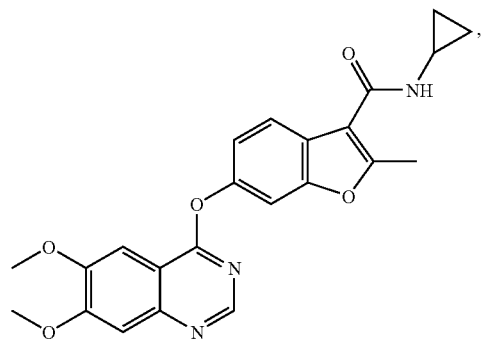

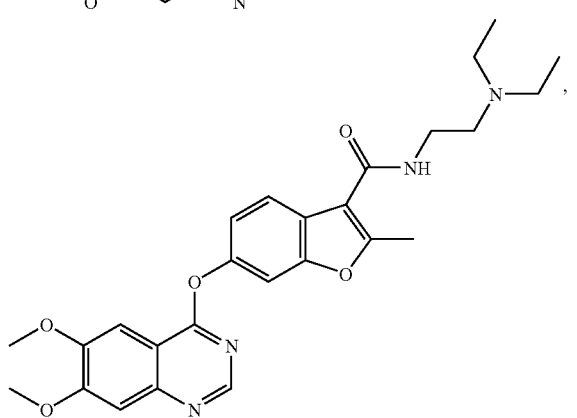

-continued

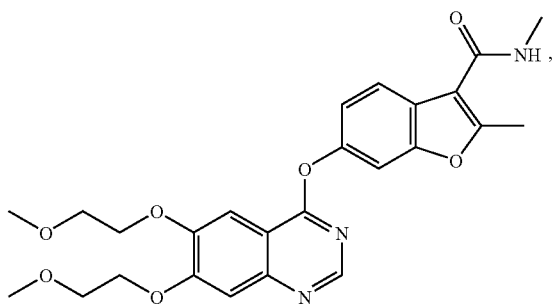

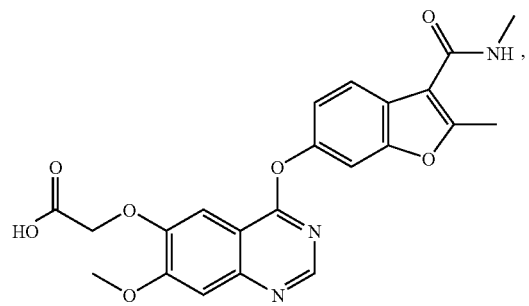

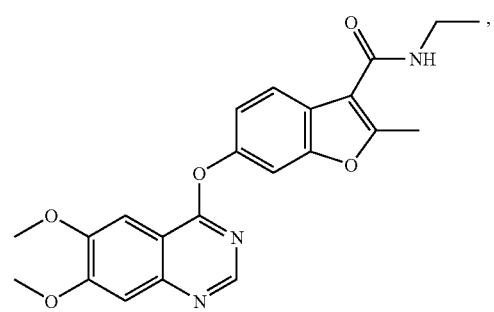

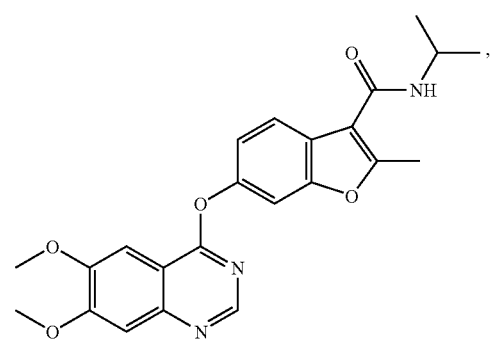

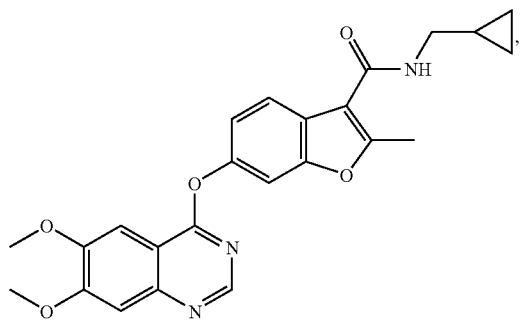

-continued

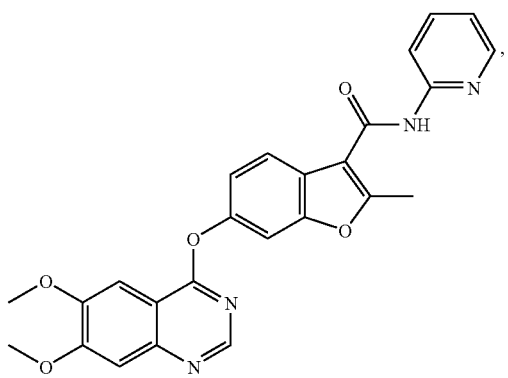

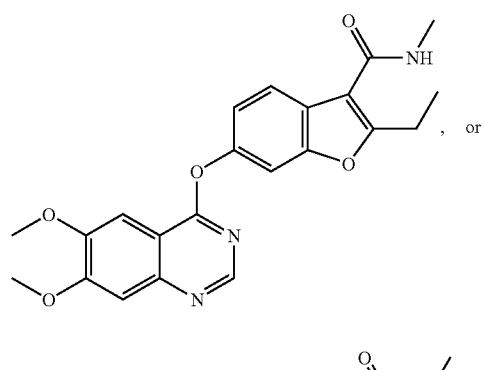

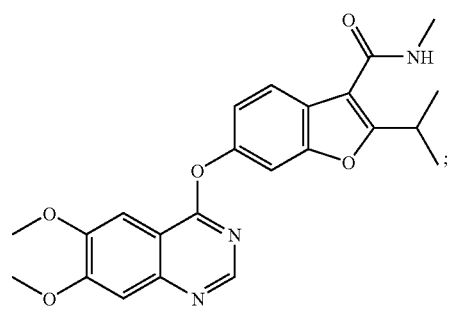

and a pharmaceutically acceptable carrier.

13. A pharmaceutical composition comprising a compound of the following formula:

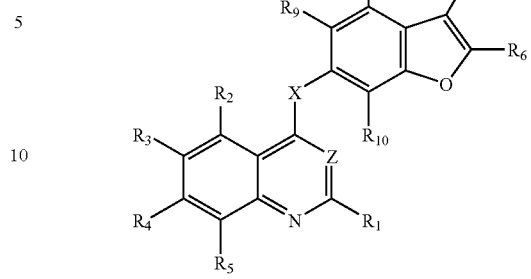

wherein
each of $R_1$, $R_2$, $R_3$, $R_4$, $R_5$, $R_8$, $R_9$, and $R_{10}$, independently, is H, halo, amino, hydroxy, alkyl, alkenyl, alkynyl, heterocycloalkyl, alkoxy, alkylthio,-carboxy, alkoxycarbonyl, carbonylamino, or sulfonylamino, or $R_3$ and $R_4$, together with the carbon atoms to which they are attached, form a 4- to 7-membered saturated, unsaturated, or aromatic ring, optionally containing 1-3 hetero atoms selected from N, O and S;
$R_6$ is alkyl;
$R_7$ is —C(O)NR$_a$R$_b$, each of R$_a$ and R$_b$, independently, being H, alkyl, alkenyl, alkynyl, aryl, cycloalkyl, heterocycloalkyl, or heteroaryl, or R$_a$ and R$_b$, together with the nitrogen atom to which they are attached, represent a 3-8 membered ring containing 1-3 heteroatoms;
X is O; and
Z is N;
wherein each of alkyl, alkenyl, alkynyl, cycloalkyl, heterocycloalkyl, aryl, heteroaryl and alkoxy is optionally substituted with at least one substituent chosen from halo, hydroxyl, amino, cyano, nitro, mercapto, alkoxycarbonyl, amido, carboxy, alkanesulfonyl, alkylcarbonyl, carbamido, carbamoyl, carboxyl, thioureido, thiocyanato, sulfonamido, alkyl, alkenyl, alkynyl, alkoxy, aryl, heteroaryl, cycloalkyl, and heterocycloalkyl;
and a pharmaceutically acceptable carrier.

14. The compound of claim 2, wherein $R_6$ is optionally substituted methyl.

15. The compound of claim 14, wherein $R_6$ is methyl.

16. The compound of claim 7, wherein $R_6$ is optionally substituted methyl.

17. The compound of claim 16, wherein $R_6$ is methyl.

* * * * *

UNITED STATES PATENT AND TRADEMARK OFFICE
CERTIFICATE OF CORRECTION

PATENT NO.       : 7,829,574 B2                          Page 1 of 2
APPLICATION NO.  : 12/118019
DATED            : November 9, 2010
INVENTOR(S)      : Wei-Guo Su et al.

It is certified that error appears in the above-identified patent and that said Letters Patent is hereby corrected as shown below:

On the Title Page, Item (57), in the Abstract, line 3, in the structure:

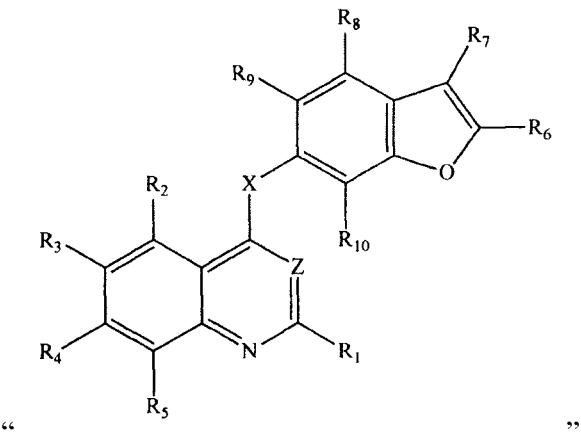

"                                            "

should read

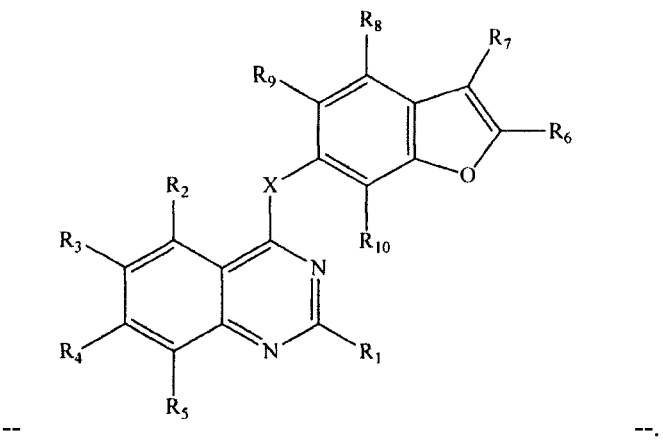

--                                           --.

In claim 1, column 13, line 29, "alkylthio,-carboxy," should read
--alkylthio, carboxy,--.

Signed and Sealed this
Fifteenth Day of March, 2011

David J. Kappos
*Director of the United States Patent and Trademark Office*

CERTIFICATE OF CORRECTION (continued)
U.S. Pat. No. 7,829,574 B2

In claim 2, column 13, line 67, "alkylthio,-carboxy," should read --alkylthio, carboxy,--.

In claim 11, column 17, line 1, "alkylthio,-carboxy," should read --alkylthio, carboxy,--.

In claim 11, column 17, line 17, "carbamide," should read --carbamido,--.

In claim 13, column 20, line 19, "alkylthio,-carboxy," should read --alkylthio, carboxy,--.